US012714610B2

(12) United States Patent
Erickson

(10) Patent No.: US 12,714,610 B2
(45) Date of Patent: Aug. 25, 2026

(54) GARMENT FOR LIMB WITH PADDED DIGIT PORTIONS

(71) Applicant: MEDI USA, L.P., Whitsett, NC (US)

(72) Inventor: Jody Erickson, Hillsborough, NC (US)

(73) Assignee: Medi USA, L.P., Whitsett, NC (US)

( * ) Notice: Subject to any disclaimer, the term of this patent is extended or adjusted under 35 U.S.C. 154(b) by 0 days.

(21) Appl. No.: 18/671,689

(22) Filed: May 22, 2024

(65) Prior Publication Data

US 2025/0360030 A1 Nov. 27, 2025

(51) Int. Cl.

| | |
|---|---|
| ***A61F 13/10*** | (2006.01) |
| ***A41D 19/015*** | (2006.01) |
| ***A61F 13/08*** | (2006.01) |

(52) U.S. Cl.
CPC ........ *A61F 13/08* (2013.01); *A41D 19/01523* (2013.01); *A61F 13/10* (2013.01)

(58) Field of Classification Search
CPC ............ A41D 19/002; A41D 19/01523; A41D 19/01582; A41D 19/01594; A61F 13/10; A61F 13/08
See application file for complete search history.

(56) References Cited

U.S. PATENT DOCUMENTS

| | | | | |
|---|---|---|---|---|
| 5,809,571 A * | 9/1998 | Spitzer | A63B 71/148 2/163 |
| 2007/0101474 A1* | 5/2007 | Skottheim | A41D 13/0506 2/69 |
| 2008/0125688 A1* | 5/2008 | Kellogg | A61F 13/10 602/61 |
| 2008/0282445 A1* | 11/2008 | Taliento | A41D 19/01523 2/163 |
| 2010/0024088 A1* | 2/2010 | Griefer | A41D 13/08 2/163 |
| 2012/0011633 A1* | 1/2012 | Van Hale | A41D 19/002 2/169 |
| 2020/0214370 A1* | 7/2020 | Kakadelas | A41D 13/08 |
| 2022/0395403 A1* | 12/2022 | Lipshaw | A61H 7/001 |

OTHER PUBLICATIONS

Definition of "pocket" from Britannica Dictionary. Accessed from https://www.britannica.com/dictionary/pocket on Nov. 26, 2025. (Year: 2025).*

* cited by examiner

*Primary Examiner* — Patrick J. Lynch
*Assistant Examiner* — Brianna T. Duckworth
(74) *Attorney, Agent, or Firm* — Rimon PC

(57) ABSTRACT

The present invention relates to a compression garment for hands or feet with padding between digits to provide compression to digits. The compression garment has a body with an open front and separating walls to create space for digits to fit through. A pocket is created by a set of separating walls between digits and a padding piece is removably inserted into the pocket to provide compression to digits.

19 Claims, 8 Drawing Sheets

106
103

202
200

GARMENT FOR LIMB WITH PADDED DIGIT PORTIONS

BACKGROUND

Edema is a well-documented condition involving tissue swelling caused by excess fluid trapped in body tissues. Edema can affect any part of the body, but it is most frequently exhibited and noticed in limbs. Causes of edema include pregnancy, medicines, and diseases such as congestive heart failure, kidney diseases, venous insufficiency, lymphedema, liver cirrhosis, among a variety of other conditions.

The use of compression garments to combat and manage edema is well-known. Compression garments are worn on limb areas where edema is present or may form. Edema is typically exhibited in limbs, hands, and feet, but edema also affects digits, or fingers and toes, and compression exerting on digits helps manage edema in these areas.

Exerting proper therapeutic amounts of compression on digits to address and manage edema remains a significant obstacle in the art. Since limbs are of substantial volume and structural singularity, exerting compression can be achieved with various means to exert pressure. By contrast, providing therapeutic levels of compression to digits is complicated due to a variety of issues, including volume, shape, distance between digits, converging/constrained intersections with body limbs, fragility, planar alignment of individual portions requiring individualized levels of compression, loss of digit function while wrapped, among other issues. Individual wrapping and fasteners are too cumbersome to apply to each digit and limit movement and use of the digits, especially fingers. Further, compression level adjustments require removal and re-wrapping until the desired therapeutic and comfort level is achieved.

The present invention addresses these and other needs in the art.

SUMMARY

These and other embodiments, features, and advantages will become apparent to those skilled in the art when taken with reference to the following more detailed description of various exemplary embodiments of the present disclosure in conjunction with the accompanying drawings.

In often provided embodiments, there is provided a compression garment for a limb, comprising: a body comprising a top and a bottom; a digit portion covering at least a portion of fingers or toes from a base of the fingers or toes when the garment is worn; at least one pair of separating walls extending from the top to the bottom, the separating walls situated adjacent to each other; and at least one pocket created by the space between the separating walls; wherein the at least one pair of separating walls separate the digit portion into digit spaces, the digit spaces adapted to receive a digit in each of the digit spaces, and wherein the pocket is configured to removably receive at least one padding piece.

In frequently provided embodiments, there is provided a compression garment as above, wherein there are three pairs of separating walls creating three pockets and dividing the digit portion of the garment into four digit spaces. The pockets and the digit spaces being distinguishable, with the digit spaces adapted to receive a digit, for example, a finger or a toe, of a user of the garment, and the pockets are adapted to receive padding but not a digit of the user.

In often provided embodiments, there is provided a compression garment as above, wherein the compression garment is configured to be a glove.

In frequently provided embodiments, there is provided a compression garment as above, wherein the glove is configured to cover the arm to the elbow.

In often provided embodiments, there is provided a compression garment as above, wherein the glove is configured to cover the arm to the shoulder.

In frequently provided embodiments, there is provided a compression garment as above, wherein the glove further comprises a thumb portion to cover a thumb when the glove is worn.

In often provided embodiments, there is provided a compression garment as above, wherein the thumb portion is uncovered at the tip.

In frequently provided embodiments, there is provided a compression garment as above, wherein there are four pairs of separating walls creating four pockets and dividing the garment into five digit spaces.

In often provided embodiments, there is provided a compression garment as above, wherein the compression garment is configured to be a sock.

In frequently provided embodiments, there is provided a compression garment as above, wherein the sock is configured to cover the ankle.

In often provided embodiments, there is provided a compression garment as above, wherein the sock is configured to cover up to the knee.

In frequently provided embodiments, there is provided a compression garment as above, wherein the sock is configured to cover up to the thigh area.

In often provided embodiments, there is provided a compression garment as above, wherein there are multiple padding pieces and the multiple padding pieces are provided with different sizes and are made of different materials.

In frequently provided embodiments, there is provided a compression garment as above, further comprising a packaging pouch to store the at least one padding piece.

In often provided embodiments, there is provided a compression garment as above, further comprising particles between the top and the bottom of the body, the particles are configured to exert pressure onto a limb when the garment is worn on the limb.

In frequently provided embodiments, there is provided a compression garment as above, wherein the particles are in a polyhedron shape.

In often provided embodiments, there is provided a method to don a compression garment as above, comprising: inserting at least one padding piece into each of the at least one pocket using a tool (e.g., small stick); inserting a hand or foot into the garment; directing digits on the hand or foot towards the pockets; and inserting the digits into the pockets.

In frequently provided embodiments, there is provided a method as above, wherein the garment is a glove with four adjacent digit spaces and a hand is inserted into the glove.

In often provided embodiments, there is provided a method as above, wherein the garment is a sock with five adjacent digit spaces and a foot is inserted into the sock.

In frequently provided embodiments, there is provided a method to remove padding from the garment as above, comprising: grasping the at least one padding piece in the pocket; and pulling the at least one padding piece away from the garment while exerting a force on the garment to counter the pulling.

BRIEF DESCRIPTION OF THE DRAWINGS

The skilled person in the art will understand that the drawings, described below, are for illustration purposes only.

DETAILED DESCRIPTION

For clarity of disclosure, and not by way of limitation, the detailed description of the invention is divided into the subsections that follow.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, the term "and/or" may mean "and," it may mean "or," it may mean "exclusive-or," it may mean "one," it may mean "some, but not all," it may mean "neither," and/or it may mean "both."

As used herein, "digit portion" refers to a part of a garment worn on the limb that covers a part of the digits on the limb. When the garment is worn on a hand, the digit portion of the garment covers a part of the fingers. The garment is worn on a foot, the digit portion of the garment covers a part of the toes.

As used herein, "digit space" refers to a space within a garment, and when the garment is worn on a limb covering a hand or a foot, the digits, namely, the fingers or toes, are situated in the digit space.

As used herein, "separating wall" refers to a swath of material extending from the top to the bottom of a space created by the top and the bottom.

As used herein, "padding pieces" refer to flexible material pieces that can be inserted into and removed from a space.

As used herein, "pocket" or "pockets" refer to a portion of the garment formed and adapted for receiving a padding piece but are not adapted for receiving a digit of a user of the garment.

Embodiments of this invention relate to a garment for a limb covering digits on the limb and having padding between the digits. The garment can be for a hand with padding between the fingers, or for a foot with padding between the toes.

Figure 1:
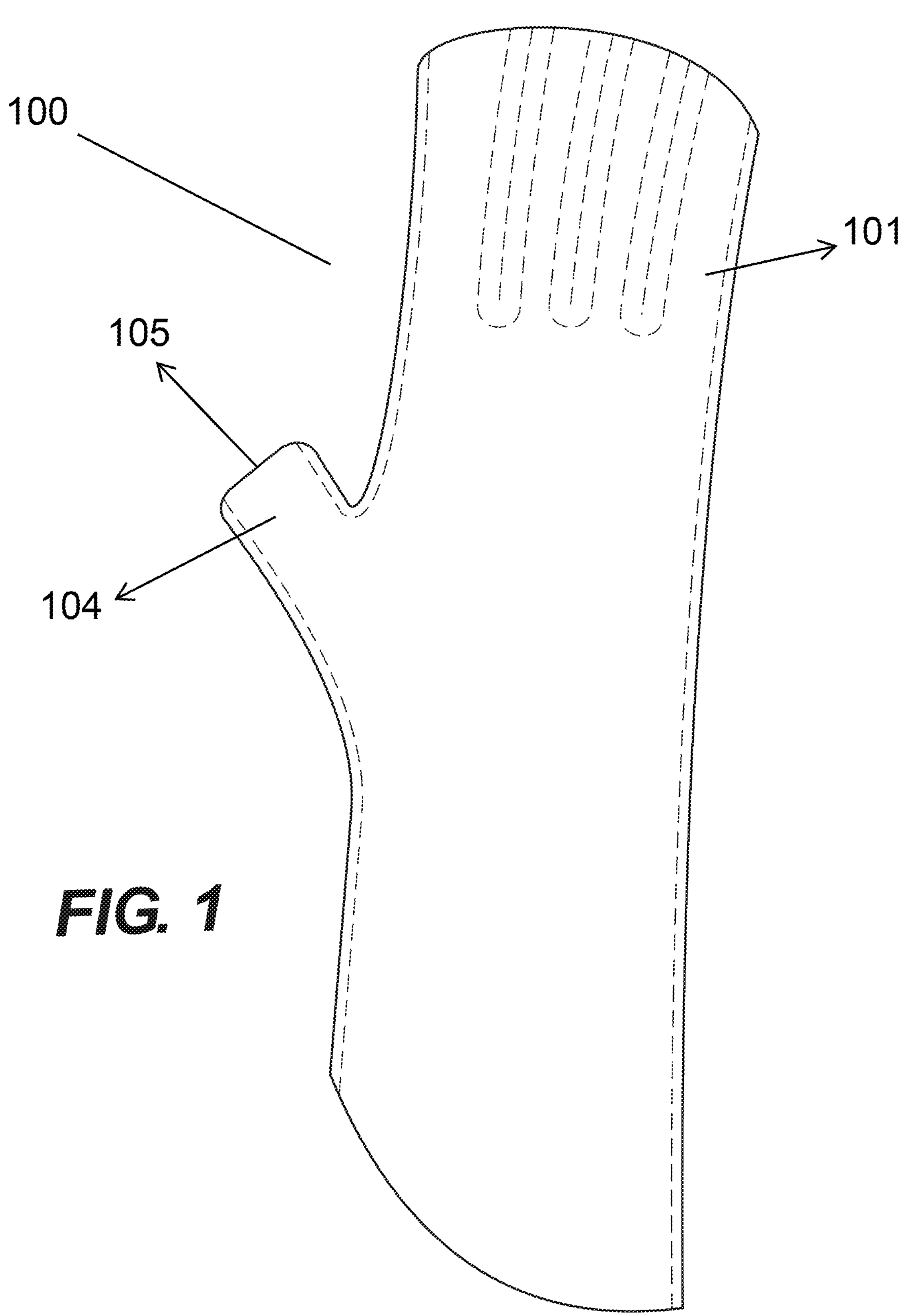
FIG. 1 illustrates a perspective view of a garment according to an embodiment herein.

FIG. 1 illustrates a perspective view of a garment according to an embodiment described herein. The garment of FIG. 1 is a glove 100 covering part of an arm near the wrist and part of a hand extending from the wrist, as well as at least part of the fingers. Glove 100 comprises a top and a bottom affixed together to form a space between them through which a hand and arm can be inserted. Top and bottom can be affixed together by various mechanisms, such as by seams, glue, sewn together, melting edges of material pieces together, or the top and bottom can be formed together in a mold. Thumb portion 104 extends from the body of the glove 100 at the side of the body, thumb portion 104 having an opening 105 for a thumb to extend out of the thumb portion 104 and enables the fingertip of the thumb to be uncovered. Digit portion 101 extends from the front of the body of the glove 100 and covers part of the fingers when the glove is worn on a hand. Digit portion 101 can cover up to the proximal interphalangeal joint, up to the distal interphalangeal joint, anywhere in between the proximal interphalangeal joint and distal interphalangeal joint or extend beyond the distal interphalangeal joint but leaves a gap for the fingertips to extend from digit portion 101. This open tip design allows access to the top part of digit portion for padding piece insertion and removal.

Figure 2:
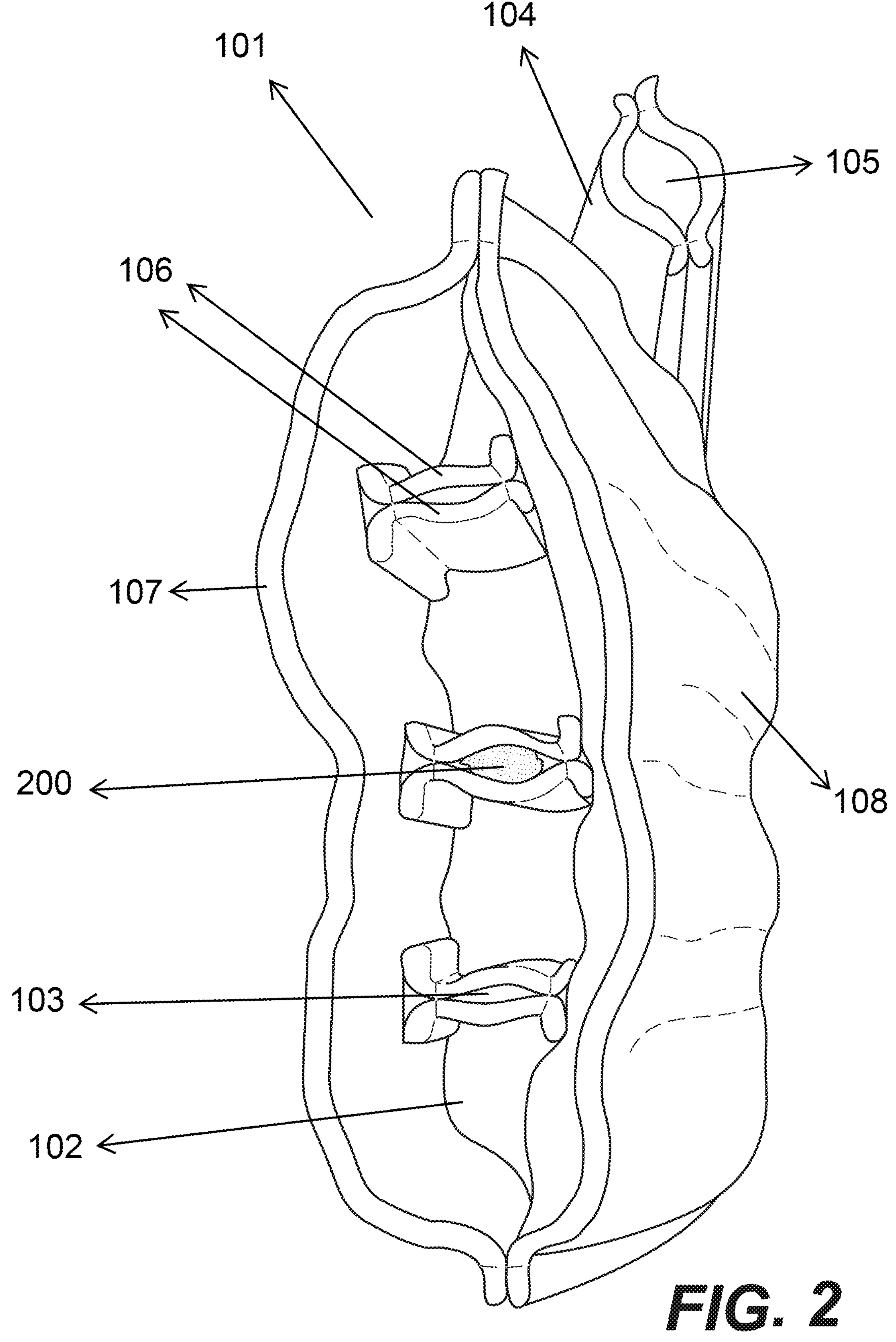
FIG. 2 illustrates a front view of the garment in FIG. 1 viewing from the digit portion of the garment.

FIG. 2 illustrates the front view of the glove at digit portion 101. On glove 100, digit portion 101 is divided into four digit spaces 102 to correspond to four fingers apart from the thumb. Digit portion 101 as shown in FIG. 2 comprises a top and a bottom connected together by a connecting mechanism, such as by a seam or by glue, and the four fingers apart from the thumb can be inserted through the space between the top and the bottom. Extending from the top to the bottom of digit portion are three sets of separating walls 106, each of the sets of separating walls 106 comprises two walls in each set situated close to each other, forming a pocket. The three sets of separating walls 106 are located in the space formed between the top and the bottom, creating digit spaces 102 between each set. With three sets of separating walls, four digit spaces 102 are created, allowing four fingers to be inserted into or through the four digit spaces 102. The sets of separating walls 106 are spaced apart from each other and from the edges of glove 100 to give appropriate space for each finger. The two middle digit spaces are often larger in volume to accommodate the middle finger and the ring finger. The digit space on the edge corresponding to the pinky finger is often smaller as compared to the other digit spaces to accommodate the small pinky finger. Similarly, digit space for the index finger may be smaller than digit space for the middle finger and ring finger.

As shown in FIG. 2, separating walls 106 extend close to the outer edge of digit portion 101 but is still within the space created by the top and the bottom. Separating walls 106 can extend along the length of digit portion 101 to line the finger length from the knuckle up to the front of digit portion 101. In some embodiments, separating walls 106 only extend along part of the length of digit portion 101, creating pockets 103 that do not cover the entire length of digit portion 101. Pockets 103 are relatively smaller than digit spaces 102. If the pockets were larger, thicker padding pieces would be required and could cause fingers to splay, which is uncomfortable. With larger pockets, especially if both ends are open, there is also a risk that the digits could be inserted into the pockets instead of the digit spaces. Larger pockets also pose the risk of having smaller padding pieces falling out.

Each pair of separating walls is attached to the top 107 and bottom 108, within each pair, the two separating walls are situated next to each other to create an open area forming pocket 103. The top 107 and the bottom 108 together form the body of the garment. In certain embodiments the top 107 and the bottom 108 are formed of a single tubular material. In other embodiments, the top 107 and the bottom 108 are formed of a single piece of material connected with a single seam or closeable connection (e.g., using hook and loop fasteners). In other embodiments, the top 107 and the bottom 108 are formed of two pieces of material connected with two or more seams or closeable connection (e.g., using hook and loop fasteners). With three pairs of separating walls, three pockets 103 are created. A padding piece 200 can be removably inserted into the open area formed by each pocket 103, thereby providing padding between the fingers when the glove 100 is worn on a hand. Padding pieces 200 can be made from flexible materials, optionally heat insulated materials. Exemplary materials suitable for padding of the glove include materials with inherent compression resilience such as foam, cloth, memory foam, cotton, gel, other elastomeric materials such as expanded rubber, compressible gas or liquid filled modules/pods, among other materials.

In certain embodiments, two separating walls in a pair create a pocket with an opening at the front of digit portion. The other ends of the two separating walls can be left separated or attached to each other to create a closed pocket. For pockets with two open ends, padding pieces can be inserted into and removed from both ends, even though inserting and removed at the end distal from the front of the digit portion requires additional maneuvering. In particular, a tool can be inserted into the glove from the end proximal to the upper arm to reach the back of a pocket to grasp padding pieces.

In some embodiments, an additional separating wall is installed next to each of the edges of digit portion to create two additional pockets. A padding piece can be inserted into the two additional pockets to provide additional compression to the fore finger and/or the pinky finger as desired. Alternatively, only one additional wall creating one additional pocket is provided. Separating walls 106 are attached to the top 107 and bottom 108 by different mechanisms, such as by sewing, glue, fasteners, by extrusion, or formed from a mold. Separating walls 106 can be removably attached to the top 107 and bottom 108 of glove 100, such that they can be removed and the glove 100 is worn without barriers between the fingers. Alternatively, separating walls 106 can be fixedly attached to the top 107 and bottom 108 of glove 100.

In certain embodiments, the top, bottom, and separating walls of the glove can be made of the same or different materials. The materials are suitable for clothing purposes and are flexible and can bend or morph to fit with a hand. Optionally, the outside of the glove is coated with a water-resistant material. Other surfaces of the top, bottom, and separating walls can also be coated with water resistant material. The materials are preferably washable and can be dried using conventional household dryers or by natural means, e.g. hanging in the sun.

In frequently included embodiments, the garment is provided with or without padding pieces. Padding pieces can be fashioned from foam, cloth, memory foam, cotton, gel, other elastomeric materials such as expanded rubber, compressible gas or liquid filled modules/pods or other flexible materials suitable for use in clothing, and thus may be procured separately. Alternatively, padding pieces may be an insert comprised of irregular pattern particles in a sealed pouch. Padding size, structure, and hardness may affect pressure exerted from padding pieces onto fingers while the glove is worn. In foam, hardness is measured by Indentation Load Deflection (ILD) or Indentation Force Deflection (IFD), which is a measurement of pressure, by pounds per cubic foot, to compress a 4-inch foam sample by 25% of its thickness. Typically, soft foams have ILD $<30 lb/ft^3$, medium foams have ILD between 30-40 $lb/ft^3$, and firm foams have ILD>40 $lb/ft^3$. For padding pieces made from foam, foam with ILD $<100 lb/ft^3$ is suitable for use as padding pieces.

In some embodiments, the garment is provided with a set of padding pieces of various thicknesses and/or made of various materials. A user can choose among the padding pieces provided for the best fit with the user's hands and fingers, the level of compression to be applied, as well as the user's condition. Users with thinner fingers may need thicker padding pieces to exert the same pressure onto their fingers as compared to users with thicker fingers. Padding pieces can also be procured using available items from households, such as foam pieces or cloth pieces.

Padding pieces have lengths that fit with the lengths of the pocket measured along the digits. Length of the padding pieces can be, for example, equal to, or between 80% to 100% of the length of the pocket. Shorter padding pieces are contemplated. Padding pieces can also be longer than the pockets and folded to adjust thickness and length to fit with the pockets. Generally, the pockets are of the same length, but in some cases, the pockets are of different lengths, such as the pockets adjacent to the little finger may have a shorter length. In that case, padding pieces provided for that pocket would be sized differently to fit that pocket. Pressure exerted by padding pieces on fingers and/or toes upon insertion of padding pieces into pockets is in the range of 5-30 mmHg, preferably 10-20 mmHg. Changing the various padding pieces gives different compression levels, and a user can choose and change the padding pieces from a collection of padding pieces for the right compression level for their need.

Figure 3:
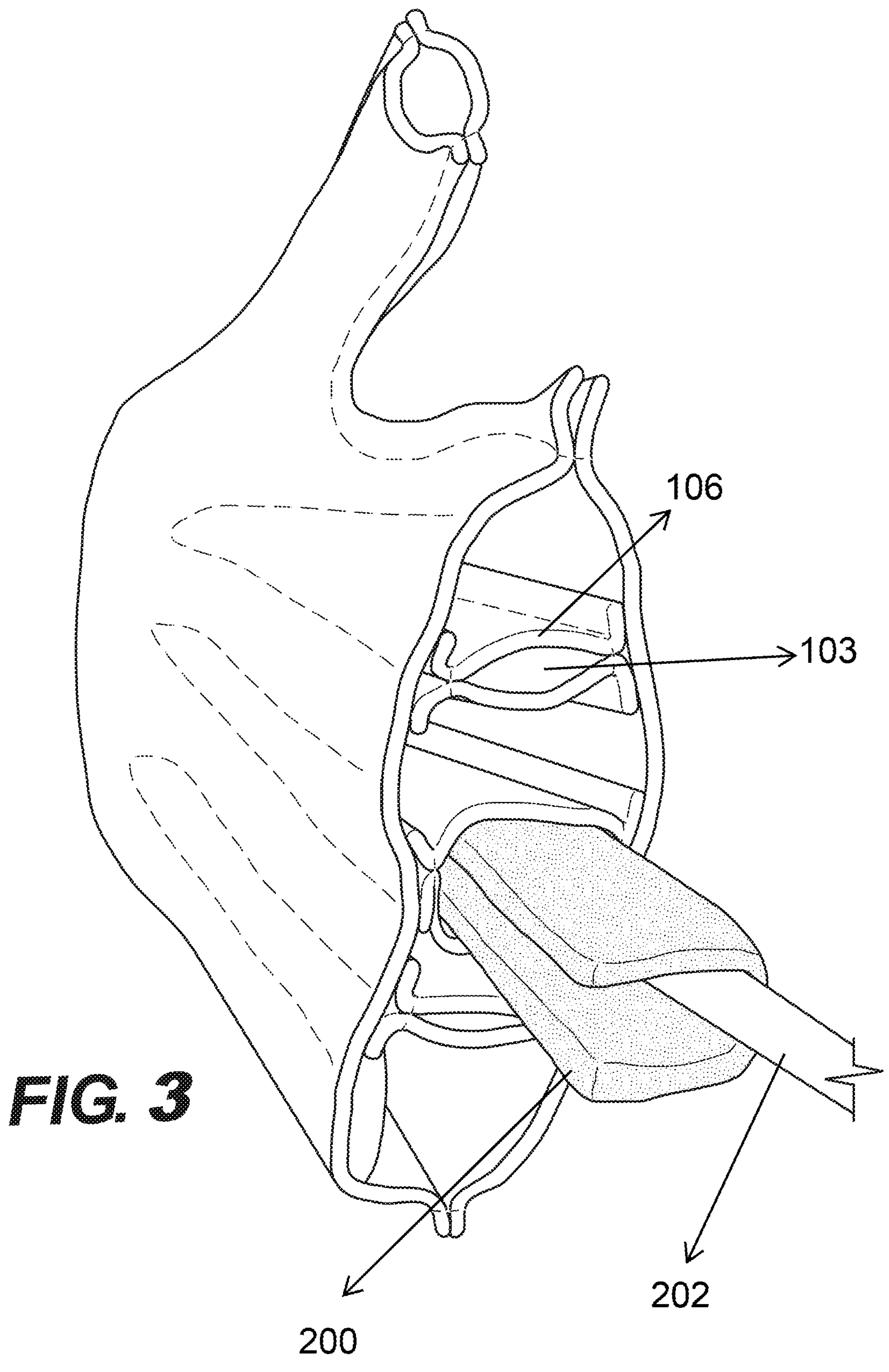
FIG. 3 illustrates installing padding between digit portions of the garment.

FIG. 3 illustrates the steps taken to install a padding piece 200 into pocket 103. As shown in FIG. 3, an exemplary tool 202 is used to push padding piece 200 into pocket 103. Padding piece 200 in this case is a piece of foam fashioned into a U shape. Tool 202 is, for example, a stiff, long, small stick or stick-like apparatus (e.g., rod, dowel or skewer), which can be a tool/spoon/utensil handle, tweezers, alligator clamp, hemostat, plyers or similar, and is placed into the U shape foam piece to push the foam piece into pocket 103. As used herein the term "tool" refers to such stick, stick-like apparatus (e.g., rod, dowel or skewer), tool/spoon/utensil handle, tweezers, alligator clamp, hemostat, plyers or similar. Upon installation, padding piece 200 fits snuggly into pocket 103 between two separating walls 106.

Other padding pieces shaped differently may be used. A foam piece shaped like a rectangular beam is also suitable for use. A piece of cloth can be stuffed into the pockets for used as padding. Materials that are ergonomic forming can also be used, such that the padding pieces form to the contour of the digits. Padding materials can be heat sensitive, such that padding pieces form to the contour of the digits when exposed to heat from the digit. Other shapes for the padding piece are contemplated.

Figure 4:
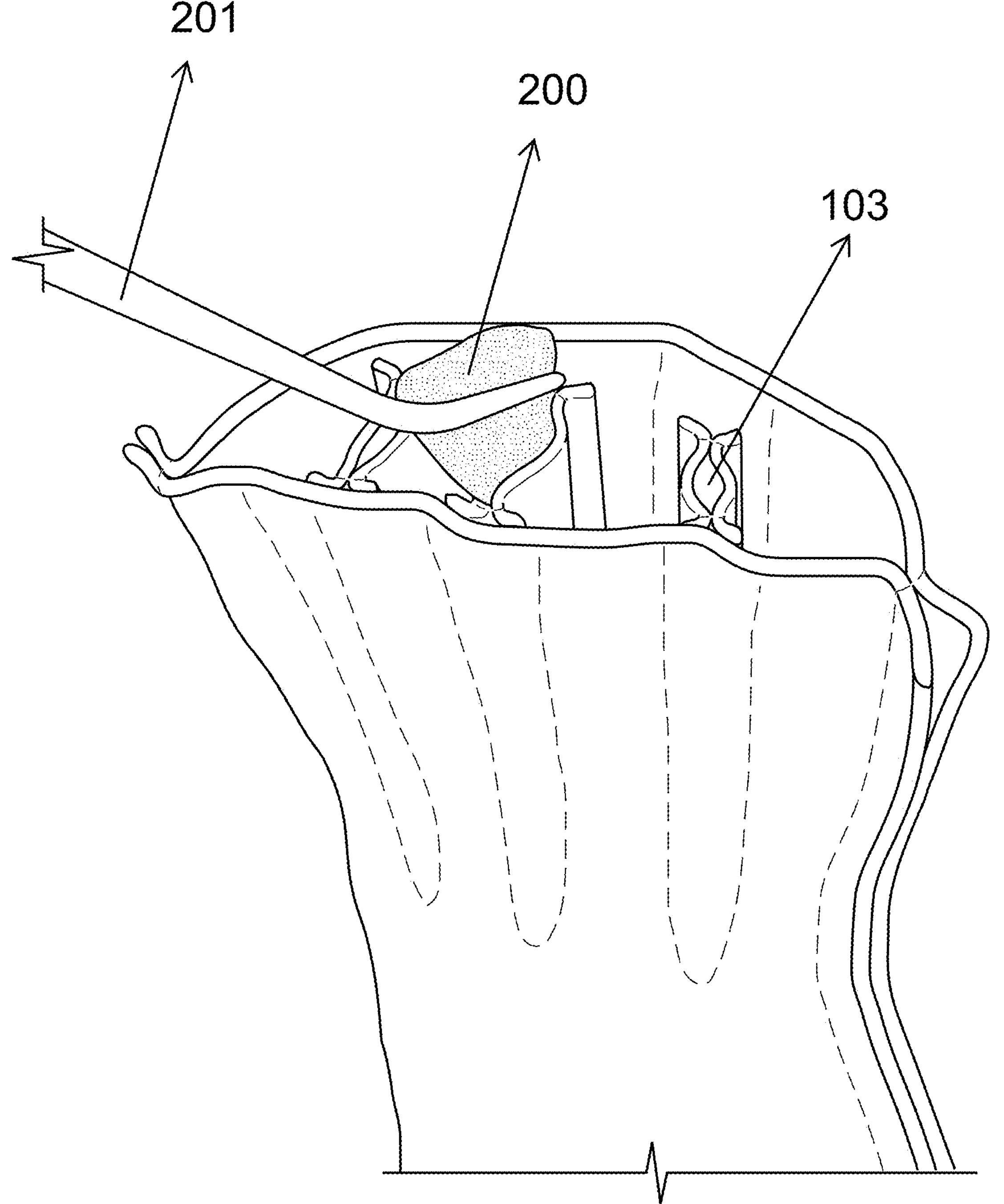
FIG. 4 illustrates removing padding between digit portions from the garment.

FIG. 4 illustrates the steps taken to remove padding piece 200 from pocket 103. A pair of tweezers 201 is used to grasp padding piece 200 from pocket 103 and pull padding piece 200 out. Padding pieces 200 are installed into pocket 103 only by being inserted into the space forming pocket 103, and thus is easily removable. In some cases, a user can use their fingertips to grasp the end of padding piece 200 and pull it out. In other cases, a user can use a tool with a hood at an end or tweezers to pull the padding piece 200 out of pocket 103 before it can be grasped by human fingers.

In certain embodiments, padding pieces are provided with the garment and a storage pouch is provided with padding pieces in a kit. A user can store various padding pieces in the storage pouch and take out padding pieces suitable for the use at the time. For example, thicker padding pieces are used when more pressure exerted onto the fingers is desired. Thinner padding pieces are used when less pressure exerted onto the fingers is desired.

Figure 5:
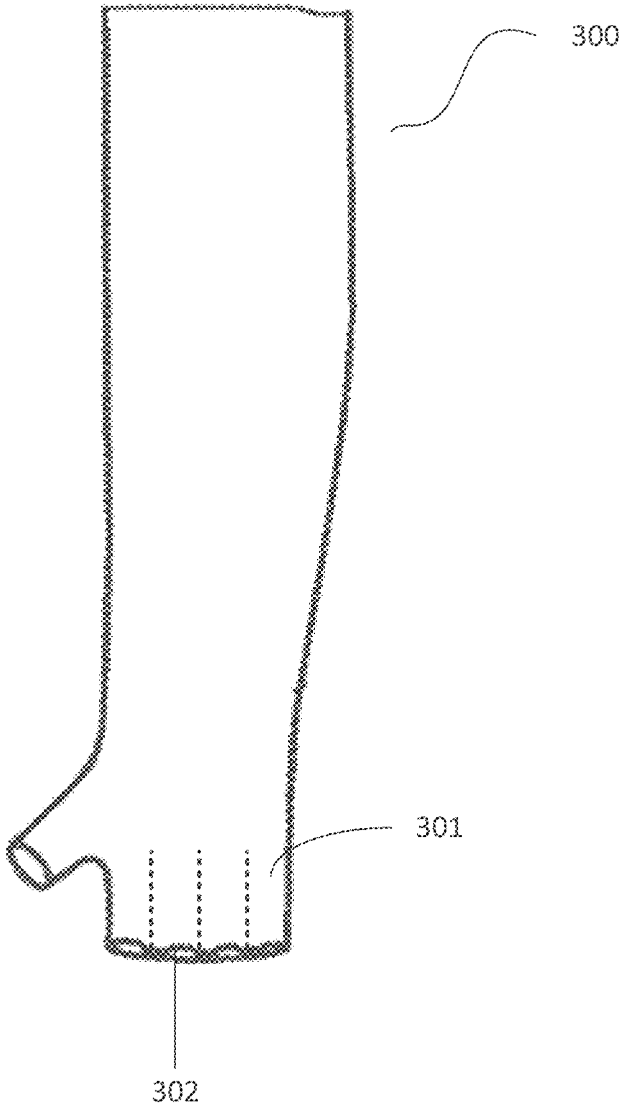
FIG. 5 illustrates a garment for an arm according to embodiments herein.

FIG. 5 illustrates an embodiment of the garment herein. The garment 300 is a glove extending to cover the forearm up to the elbow. The garment has digit portion 301 divided into four digit spaces 302, with three pairs of separating walls creating four digit spaces in digit portion 301. Each of the three pairs of separating walls create a pocket wherein padding pieces can be fitted. When a user wears this garment 300, compression is exerted onto the forearm, the hand, and the fingers of the user.

Figure 6:
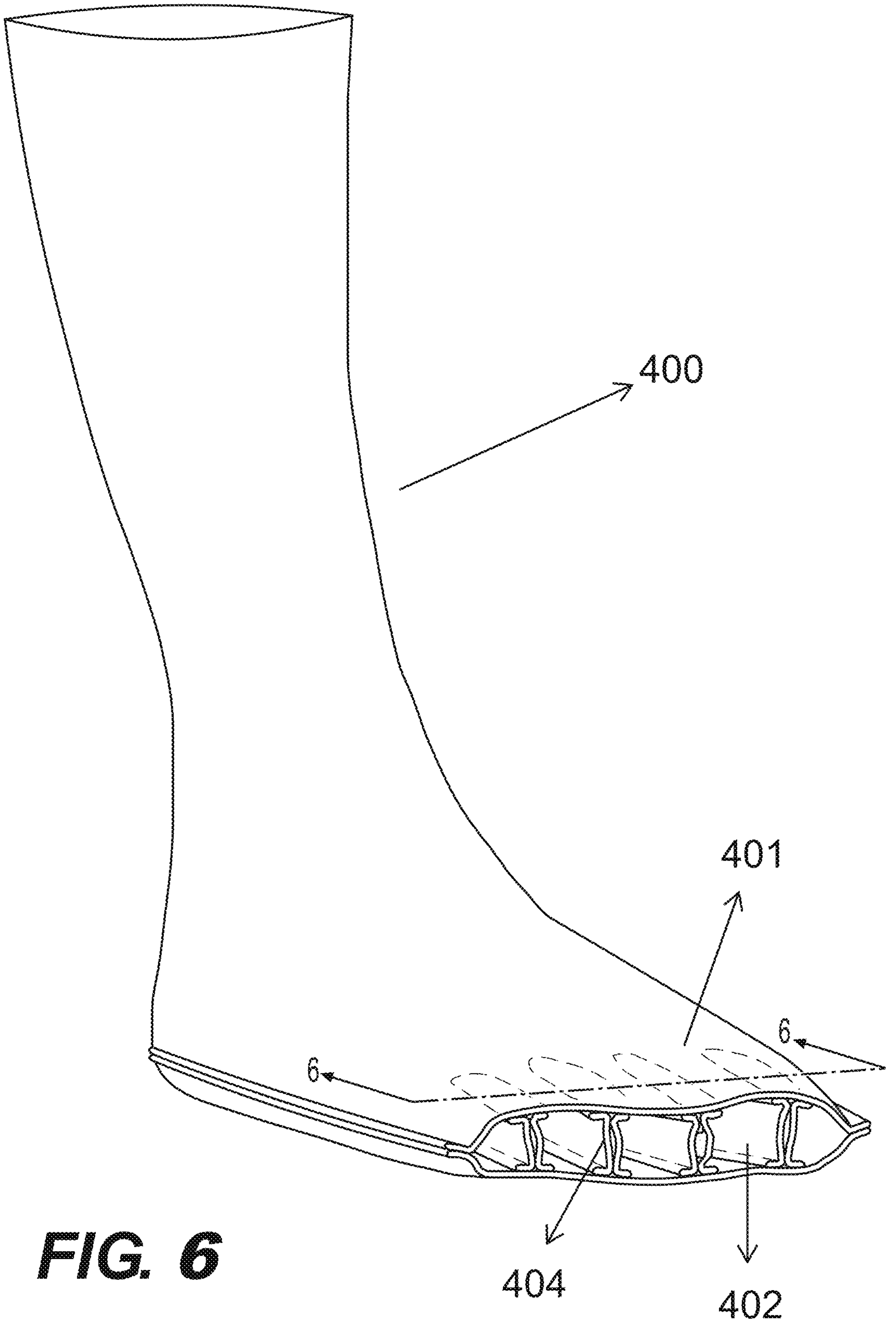
FIG. 6 illustrates a garment for a leg according to embodiments herein.

FIG. 6 illustrates another embodiment of the garment herein. The garment is a sock 400 extending up the calf of a user and covering the feet and part of the toes of the user. The sock 400 only covers part of the toes when worn, and the tip of the toes are exposed outside, optionally including the toenails. The sock 400 can extend up the calf and cover a portion of the calf, up to the knee area, or into the thigh area to exert compression to different areas of the leg as needed.

Figure 7:
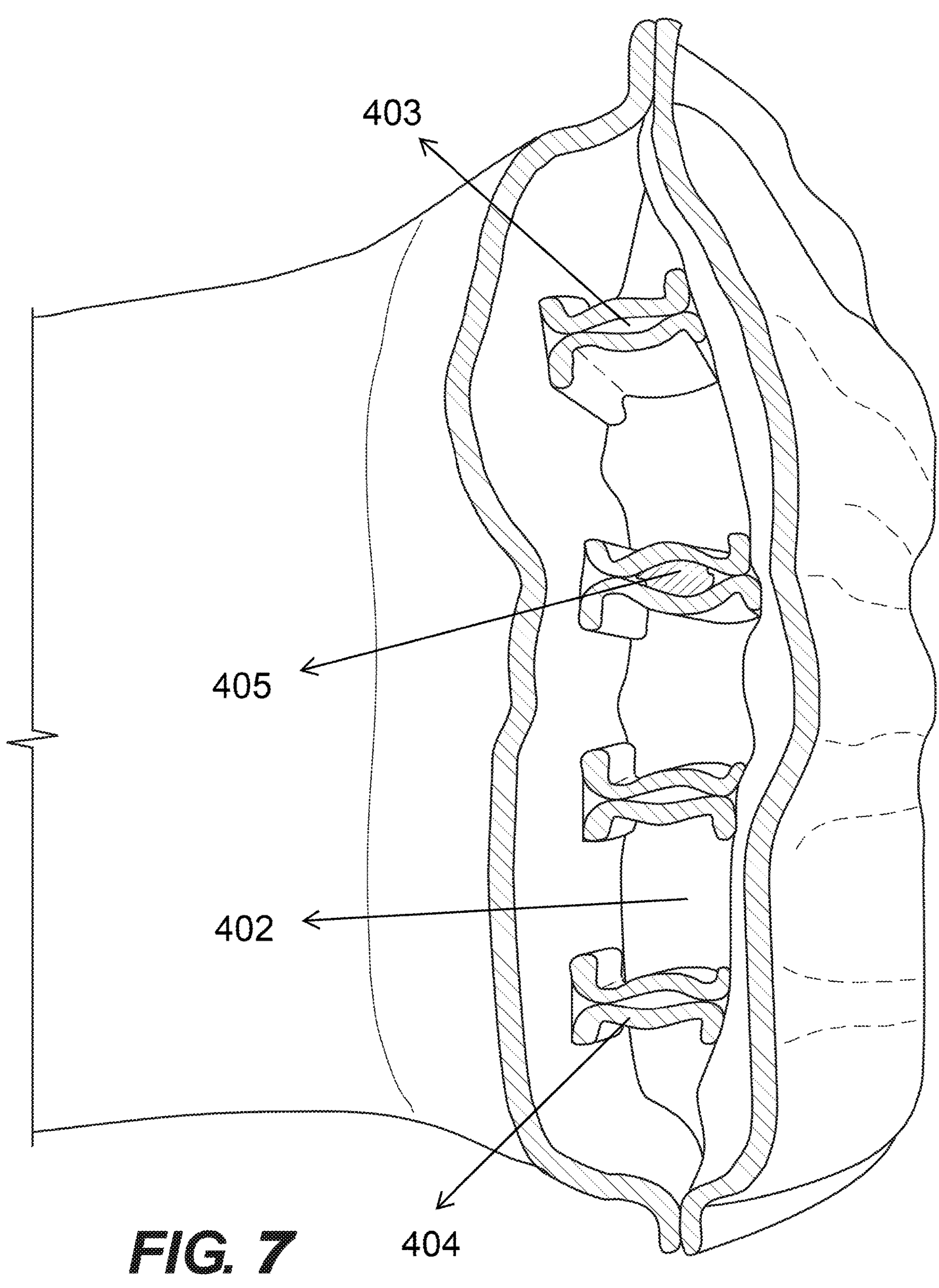
FIG. 7 illustrates a front view of the garment in FIG. 6 viewing from the digit portion of the garment.

FIG. 7 illustrates a front view of the sock 400 in FIG. 6 at the digit portion. In digit portion 401 of the sock 400, four pairs of separating walls 404, forming four pockets 403, extend from the top 406 of the sock to the bottom 407 of the sock, creating five digit spaces 402 for five toes to fit in. Each pair of separating walls 404 are adjacent to each other and create a pocket 403 in between, wherein padding pieces 405 can fit. Padding pieces 403 are removable using the same technique as for the glove and can be provided with the sock 400 or can be fashioned by each user. The top 406 and the bottom 407 together form the body of the garment. In certain embodiments the top 406 and the bottom 407 are formed of a single tubular material. In other embodiments, the top 406 and the bottom 407 are formed of a single piece of material connected with a single seam or closeable connection (e.g., using hook and loop fasteners). In other embodiments, the top 407 and the bottom 407 are formed of two pieces of material connected with two or more seams or closeable connection (e.g., using hook and loop fasteners).

Padding pieces can be provided with socks according to embodiments herein. Padding pieces are fashioned to fit with toes and pockets between toes, therefore padding pieces are smaller. Padding pieces for socks can be made of similar materials to padding pieces for gloves.

In some embodiments, the top and/or bottom of the garment provide compression to a limb on which the garment is worn. In any or all of the embodiments described herein, the top and/or bottom of the garment body may be made of elastic material, which stretches around the limb (when donned) to provide compression. A layer of foam material, e.g., in the form of padded body material, may be provided in between the top and bottom of the garment, which provides localized pressure variance due to compressing the irregular surface against the skin. In certain embodiments the body material, or padded body material includes one or more adjustable strap or closure adapted to wrap around at least part of the oversleeve to exert compression on the limb. In certain embodiments, an additional elastic oversleeve can be applied over the elastic material to provide additional compression. In certain embodiments the oversleeve is a tubular garment comprised of elastic material. Also, in certain embodiments the oversleeve includes one or more adjustable strap or closure adapted to wrap around at least part of the oversleeve to exert compression on the limb. According to embodiments provided herein, compression levels are therapeutic compression levels adapted to the limb being treated and the underlying medical condition. Such compression levels are predetermined and measured or measurable such that a user of the garment can apply the predetermined compression level when donning the garment and/or utilizing straps, closures, and/or an oversleeve. In certain embodiments a pneumatic compression sleeve is provided that is adapted to be placed over a garment described herein after the garment has been donned, the pneumatic compression sleeve providing compression to the limb.

In some embodiments, the top and/or bottom are formed of material containing particles to provide padding in the body material such that the garment has padding along the top and/or bottom. Stated differently, the garment may be formed at least partially of a body material that contains particles providing padding, which type of body material is also referred to herein as a padded body material. In one such exemplary embodiment, the top and bottom of the body are provided, e.g., affixed together as described herein or in tubular form, thereby forming the garment, with the particles sandwiched and trapped within the body material. Most often the body material is formed containing particles in a manner such that the particles are non-removable.

Particles used within the padded body material can be made from different materials. Foam particles, in particular plastic foam particles, are suitable for inclusion within the padded body material. Particles can be of various shapes, such as cubic, tetrahedrons, cuboctahedrons, or other polyhedron shapes. The presence of particles in these embodiments provides an irregular pattern pressure exerted onto the limb when the garment is worn on the limb. Pressure exerted onto the hand by these particles are contemplated to be between 5-30 mmHg, preferably 10-20 mmHg.

Figure 8:
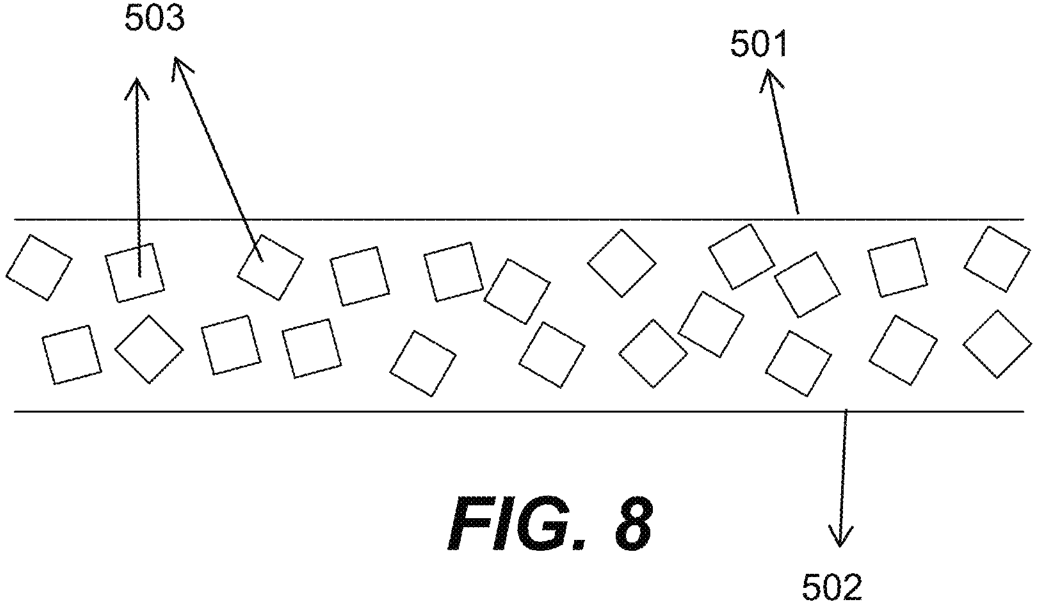
FIG. 8 is a cross section view of a body layer of a compression garment according to an embodiment herein.

FIG. 8 illustrates a cross section of body material (e.g., the top and/or bottom) containing foam particles. Foam particles 503 are present in between the two layers 501, 502 of the body material. Foam particles 503 as shown herein are in cuboid shape and are stuffed into the space between the two layers 501, 502 of the padded body material at random to create an irregular pressure pattern exerted onto a limb when the garment is worn on the limb.

The compression garment according to embodiments herein are made by a cut and sew process. Parts can also be held together by other affixing methods, such as by heat, glue, fasteners, hook and loop fasteners, zippers, buttons or button-like closures, slide closures, or other suitable attachment mechanisms. Some parts are manufactured by extrusion or molding.

In a first embodiment, a compression garment for a limb is provided, the compression garment comprises: a body comprising a top and a bottom; a digit portion covering at least a portion of fingers or toes from a base of the fingers or toes when the garment is worn; at least one pair of separating walls extending from the top to the bottom and along the length of the digit portion, the separating walls situated adjacent to each other; and at least one pocket created by the space between the separating walls, wherein the at least one pair of separating walls separate the digit portion into digit spaces, the digit spaces adapted to receive a digit in each of the digit spaces, and wherein the pocket is configured to removably receive at least one padding piece.

In a second embodiment, the first embodiment includes there are three pairs of separating walls creating three pockets and dividing the garment into four digit spaces.

In a third embodiment, the first embodiment includes the compression garment is configured to be a glove.

In a fourth embodiment, the first embodiment includes the glove is configured to cover the arm to the elbow.

In a fifth embodiment, the first embodiment includes wherein the glove is configured to cover the arm to the shoulder.

In a sixth embodiment, the first embodiment includes the glove further comprises a thumb portion to cover a thumb when the glove is worn.

In a seventh embodiment, the first embodiment includes the thumb portion is uncovered at the tip.

In an eighth embodiment, the first embodiment includes four pairs of separating walls creating five pockets and dividing the garment into five digit spaces.

In a ninth embodiment, the first embodiment includes the compression garment is configured to be a sock.

In a tenth embodiment, the ninth embodiment includes the sock is configured to cover the ankle.

In a eleventh embodiment, the ninth embodiment includes the sock is configured to cover up to the knee.

In a twelfth embodiment, the ninth embodiment includes the sock is configured to cover up to the thigh area.

In a thirteenth embodiment, the first embodiment includes there are multiple padding pieces and the multiple padding pieces are provided with different sizes and are made of different materials.

In a fourteenth embodiment, the first embodiment further comprises a packaging pouch to store the at least one padding piece.

In a fifteenth embodiment, the first embodiment further comprises particles between the top and the bottom of the body, the particles are configured to exert pressure onto a limb when the garment is worn on the limb.

In a sixteenth embodiment, the fifteenth embodiment includes the particles are in a polyhedron shape.

In a seventeenth embodiment, a method to don a garment of the first embodiment is provided, comprising: inserting at least one padding piece into each of the at least one pocket using a tool (e.g., small stick); inserting a hand or foot into the garment; directing digits on the hand or foot towards the pockets; and inserting the digits into the pockets.

In an eighteenth embodiment, the seventeenth embodiment includes the garment is a glove with four adjacent digit spaces and a hand is inserted into the glove.

In a nineteenth embodiment, the seventeenth embodiment includes the garment is a sock with five adjacent digit spaces and a foot is inserted into the sock.

In a twentieth embodiment, a method to remove a garment of the first embodiment is provided, comprising: grasping the at least one padding piece in the pocket; and pulling the at least one padding piece away from the garment while exerting a force on the garment to counter the pulling.

In a twenty first embodiment, the fifteenth or sixteenth embodiments provide a body material formed of a padded body material.

In a twenty second embodiment, any of the first through the twenty first embodiments are provided, where the garment further comprises one or more closure or strap adapted to wrap at least partially around the garment to provide a predetermined level of compression to the limb after the garment is donned.

In a twenty third embodiment, any of the first through the twenty second embodiments are provided, where the garment is provided in a system further comprising a pneumatic compression sleeve, or for use together with a pneumatic compression sleeve, wherein the pneumatic compression sleeve is adapted to wrap around the garment.

Citation of the above publications or documents is not intended as an admission that any of the foregoing is pertinent prior art, nor does it constitute any admission as to the contents or date of these publications or documents.

I claim:

1. A compression garment for a limb, comprising:

a body comprising a top and a bottom adapted to provide a compressive force to the limb;

a digit portion covering at least a portion of fingers or toes from a base of the fingers or toes when the garment is worn;

at least one pair of separating walls extending from the top to the bottom and along the length of the digit portion, the separating walls situated adjacent to each other with a space between the separating walls; and at least one pocket with an opening at a distal region of the digit portion created by the space between the separating walls;

wherein the at least one pair of separating walls separate the digit portion into digit spaces, the digit spaces adapted to receive a digit in each of the digit spaces, wherein the at least one pocket is configured to removably receive at least one padding piece such that when the garment is worn and at least one padding piece is received in the at least one pocket an additional compressive force is applied to the digit, and wherein the distal region of the digit portion is located distally from an area of the compression garment covering knuckles when the compression garment is worn.

2. The compression garment of claim 1, wherein there are three pairs of separating walls creating three pockets and dividing the digit portion of the garment into four digit spaces.

3. The compression garment of claim 1, wherein the compression garment is configured to be a glove.

4. The compression garment of claim 3, wherein the glove is configured to cover the arm to the elbow.

5. The compression garment of claim 3, wherein the glove is configured to cover the arm to the shoulder.

6. The compression garment of claim 3, wherein the glove further comprises a thumb portion to cover a portion of a thumb when the glove is worn.

7. The compression garment of claim 6, wherein the thumb portion is open at a tip and enables the fingertip of the thumb to be uncovered when the glove is worn.

8. The compression garment of claim 1, wherein there are four pairs of separating walls creating five pockets and dividing the digit portion of the garment into five digit spaces.

9. The compression garment of claim 1, wherein the compression garment is configured to be a sock.

10. The compression garment of claim 9, wherein the sock is configured to cover the ankle.

11. The compression garment of claim 9, wherein the sock is configured to cover up to the knee.

12. The compression garment of claim 9, wherein the sock is configured to cover up to the thigh area.

13. The compression garment of claim 1, further comprising particles within the top and the bottom of the body, the particles are configured to exert pressure onto a limb when the garment is worn on the limb.

14. The compression garment of claim 13, wherein the particles are in a polyhedron shape.

15. A method to don a garment of claim 1, comprising: inserting at least one padding piece into each of the at least one pocket using a tool; inserting a hand or foot into the garment; directing digits on the hand or foot towards the pockets; and inserting the digits into the digit spaces.

16. The method of claim 15, wherein the garment is a glove with four adjacent digit spaces and a hand is inserted into the glove.

17. The method of claim 15, wherein the garment is a sock with five adjacent digit spaces and a foot is inserted into the sock.

18. A method to remove padding from the garment of claim 1, comprising:

grasping the at least one padding piece in the pocket; and pulling the at least one padding piece away from the garment while exerting a force on the garment to counter the pulling.

19. A kit comprising the compression garment of claim 1 and multiple padding pieces, wherein the multiple padding pieces are of various sizes and made of various materials, or wherein the multiple padding pieces are of various sizes or made of various materials.

* * * * *